(12) United States Patent
Grasse et al.

(10) Patent No.: US 11,254,081 B2
(45) Date of Patent: Feb. 22, 2022

(54) PAPER PROFILE AND USE OF A PAPER PROFILE

(71) Applicant: Setter GmbH & Co. Papierverarbeitung, Emmerich (DE)

(72) Inventors: Steffen Grasse, Emmerich (DE); Roland Hulkenberg, Emmerich (DE); Leo Wins, Emmerich (DE); Franz Jochem, Emmerich (DE)

(73) Assignee: Setter GmbH & Co. Papierverarbeitung, Emmerich (DE)

( * ) Notice: Subject to any disclaimer, the term of this patent is extended or adjusted under 35 U.S.C. 154(b) by 273 days.

(21) Appl. No.: 16/082,621

(22) PCT Filed: Mar. 3, 2017

(86) PCT No.: PCT/EP2017/000286
§ 371 (c)(1),
(2) Date: Oct. 17, 2018

(87) PCT Pub. No.: WO2017/153039
PCT Pub. Date: Sep. 14, 2017

(65) Prior Publication Data
US 2019/0070823 A1    Mar. 7, 2019

(30) Foreign Application Priority Data
Mar. 7, 2016    (DE) .................. 20 2016 001413.8

(51) Int. Cl.
*B31D 5/00*       (2017.01)
*B31C 5/00*       (2006.01)
*A23G 3/56*       (2006.01)
*A43D 3/14*       (2006.01)
*A61B 13/00*      (2006.01)

(52) U.S. Cl.
CPC ........... *B31D 5/0091* (2013.01); *A23G 3/563* (2013.01); *A43D 3/1466* (2013.01); *A61B 13/00* (2013.01); *B31C 5/00* (2013.01); *Y10T 428/13* (2015.01); *Y10T 428/1303* (2015.01)

(58) Field of Classification Search
CPC ...... A23G 3/563; A43D 3/1466; A61B 13/00; B31C 5/00; B31D 5/0091; Y10T 428/13; Y10T 428/1303
See application file for complete search history.

(56) References Cited

U.S. PATENT DOCUMENTS 2,369,006 A * 2/1945 Banks ................... E04B 1/806
156/221

\* cited by examiner

*Primary Examiner* — Yan Lan
(74) *Attorney, Agent, or Firm* — Ulmer & Berne LLP; Brian Turung

(57) ABSTRACT

The invention relates to a paper profile (1), in particular for a packaging element or packaging equipment of food packaging. The paper profile (1) has an elongated shape. The paper profile (1) is formed by at least one round or almost round, flexurally rigid paper rod (3) or a plurality of round or almost round, flexurally rigid solid paper rods (3). The flexural rigidity of the paper profile (1) corresponds in at least one bending direction to the flexural rigidity of one of the rigid paper rods (3).

36 Claims, 19 Drawing Sheets

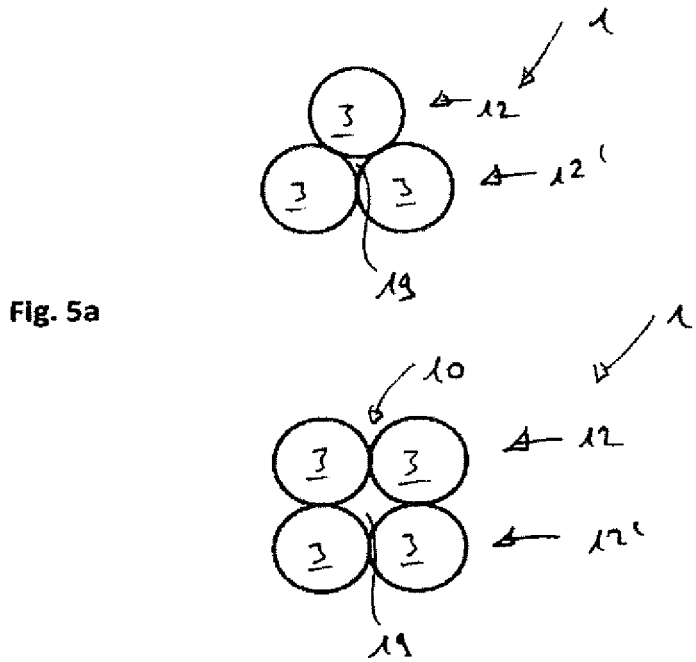
Fig. 5a
Fig. 5b
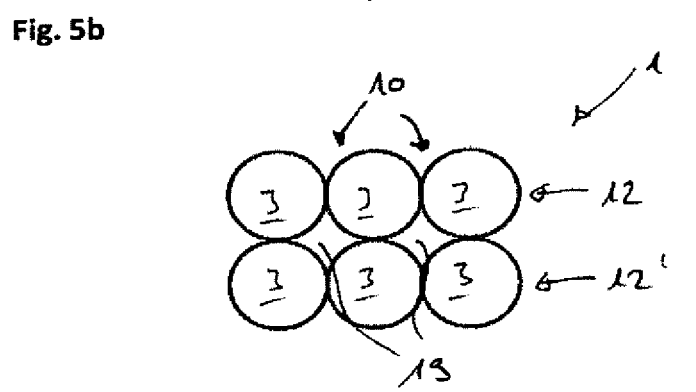
Fig. 5c
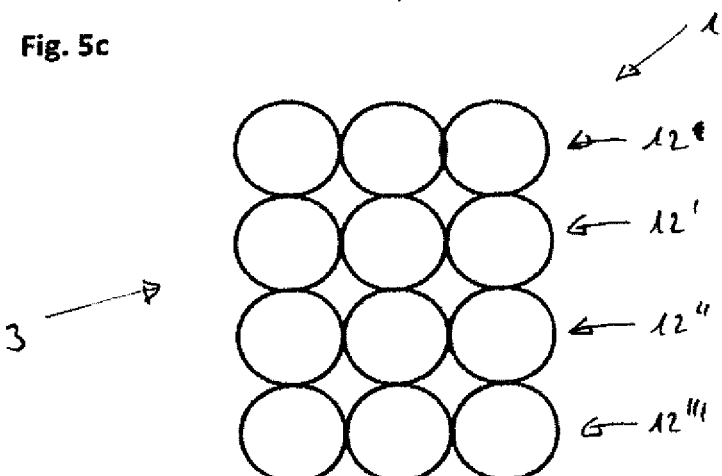
Fig. 5d

PAPER PROFILE AND USE OF A PAPER PROFILE

FIELD OF INVENTION

The invention relates to a paper profile, in particular for a packaging element or packaging equipment of food packaging, according to the first part of claim 1. The paper profile has an elongated shape. In this context, a "profile" is understood as an elongated component with an undefined cross-section, which may have a flattened shape. The profile has at least one long side in longitudinal direction, at least one narrow side in transverse direction and, as a flat profile, a profile thickness or strength in transverse direction.

The invention also concerns a procedure according to claim 10, i.e. a procedure for producing a paper profile from paper rods, in particular a paper profile described here.

The invention also relates to the use of a paper rod or a paper rod composite as defined in claims 11, 12 and 13, where the paper rod or paper rod composite may be composed in particular of a paper profile described here or according to a procedure described here.

Finally, the invention relates to an ice stick according to claim 14, a spatula according to claim 15 and a tensioning device according to claim 16.

TECHNOLOGICAL BACKGROUND

Wood is regularly used as a material in the (food) packaging industry, in the production of sanitary products and in the manufacture of medical or orthopaedic utilities. Although wood is biodegradable and/or recyclable, it can break and splinter. In addition, wood as a material can only be processed to a limited extent. For example, wood can only be coloured with limited possibilities permitted in the packaging industry, especially if the wood-based material comes into direct contact with foodstuff.

Efforts have therefore been made to industrially process a plastic material instead of a wood-based material. Plastics, however, have the considerable disadvantage that they are not biodegradable or only biodegradable with comparatively great effort, and that production as well as processing and disposal result in higher costs. Moreover, when plastic material breaks, it often produces a sharp edge, which is harmful with regard to packaging or in connection with medical purposes. In addition, plastics often contain unhealthy components which pose health risks. In many respects, plastic is therefore not a suitable alternative to wood-based materials.

DESCRIPTION OF THE INVENTION

Against this background, the problem is to specify technical arrangements to eliminate the disadvantages of wood-based materials, in particular from an environmental point of view, while avoiding the use of plastics. This problem is solved by a paper profile according to claim 1. The embodiments and/or types of the invention which solve the problem mentioned herein result from the subclaims or independent claims. The paper profile according to claim 1 is intended in particular for a packaging element, packaging material and/or packaging equipment, preferably one food packaging each. The paper profile according to the invention is preferably food-compatible, which can be achieved, for example, by the paper profile or each paper profile component comprising only paper and not an (industrial) adhesive. In this respect, the paper profile preferably consists exclusively of pulp. The paper profile may also be intended for medical, hygienic, orthopaedic and/or other consumer purposes. The paper profile has an elongated shape and is formed by at least one round or almost round, flexurally rigid paper rod or a plurality of round or almost round, flexurally rigid paper rods. Each paper rod is preferably made of a paper web; water can be used as an adhesion promoter. The paper rod has preferably no hollow space and is insofar a solid paper rod. A paper profile formed by a solid paper rod is thus a solid, i.e. void-free, paper profile. A profile formed by several rods can be formed as a solid or essentially solid profile. The diameter of a paper rod of the paper profile lies within a diameter range of about 1 mm to 12 mm, for example the diameter is about 2 mm or about 3 mm. Preferably, a restoring force, i.e. a resetting force that counteracts the bending direction, can be generated at least in certain areas by bending the paper profile. A force effect of the paper profile that generates a pretension and, in particular, influences a possible restoring force can also be provided. This can, for instance, be generated by several paper rods that are, at least in some sections, interconnected. The shape (cross-section) and/or density of the paper rods may have been altered by machining the rods during profile manufacture, for example by pressing or crimping. The flexural rigidity of the paper profile corresponds in at least one bending direction to the flexural rigidity of one of the rigid paper rods. Each rigid paper rod of the paper profile according to the invention has a flexural rigidity which has more than roughly 2 times, in particular roughly 5 times to roughly 150 times, and preferably roughly 100 times, the flexural rigidity of a similarly dimensioned paper or cardboard body, especially the flexural rigidity of a body which is not formed/manufactured from a paper web.

In this context, a rod here is understood as an elongated object with a cylindrical or almost cylindrical shape. The paper rod is made of paper, wherein a thin cardboard or a thin cardboard web may also be suitable for manufacturing the paper rod. Paper comprises a raw material containing mechanical wood pulp and/or cellulose, i.e. a material based essentially on degradable plant fibres, which is processed into a flexurally rigid (round) rod, the paper rod. Flexural rigidity here means that the paper rod—compared to wood and/or plastic—can be subjected to mechanical forces/torques without breaking or splintering, or bending or tearing, thereby forming sharp edges. Possible risks of injury in connection with the use of the profile according to the invention are therefore reduced compared to the alternatives wood or plastic. From a materials science point of view, paper appears to be softer or more flexible than wood/plastic, but in the shape/form of the paper rod described here, the material demonstrates a high strength/stability as well as a high flexural rigidity. These properties of the paper rod characterise the properties of the paper profile according to the invention, wherein the profile meets the required mechanical and/or material requirements (even for different applications).

A particular advantage arises when the paper profile should come into contact with foodstuff, for example in connection with food packaging: In many respects, paper as a material fulfils a large number of food law requirements and can be used and processed directly without special effort. In this regard, the profile according to the invention, which is formed from one (solid) paper rod or several (solid) paper rods, is also directly suitable for contact with foodstuff. From an environmental point of view, a paper profile described here can be disposed of easily, as it is degradable and can be disposed of with paper waste ("paper waste bin").

Separate disposal, for example with residual waste ("residual waste bin"), as would be the case with a wooden profile or wooden rod, is not necessary with the paper profile.

Depending on how the paper rod is processed to form the paper profile according to the invention, the flexural rigidity of the paper profile may intentionally exceed the flexural rigidity of one of the paper rods in at least one bending direction.

According to a preferred embodiment of the profile, at least one of the paper rods may be machined by pressing or flattening/crimping, wherein a type of the (solid) paper profile according to the invention is flat. Flattening means that the originally cylindrical or almost cylindrical paper rod with a round or almost round cross-section is mechanically machined so that its cross-section is oval or almost oval or flat on at least one side or on two opposite sides. The resulting profile is flat, i.e. the thickness is smaller than the dimension of the narrow side. In this variant, the profile has a flexural rigidity parallel to the narrow side of the profile, i.e. transverse to the thickness of the profile, which is higher than the flexural rigidity of the cylindrical paper rod from which the profile is formed.

Preferably, the (essentially solid) paper profile is formed from at least one layer of paper rods. This layer of paper rods (paper rod plate) contains at least two paper rods that are arranged side by side and parallel to each other. Optionally, three, four, five or more paper rods can be arranged side by side within a layer, thus forming a flat paper profile. Here, the flexural rigidity parallel to the orientation of the paper rod layer is also greater than transverse to it. In the orientation determined by the profile thickness, the flexural rigidity of the profile is essentially characterised by that of one of the rods.

If several rods are arranged within one layer, the stability of the profile is increased in at least one direction. If the stability in a second direction is also to be improved, several layers of paper rods can be arranged on top of each other. The paper profile can therefore be formed from several layers of paper rods, with at least a second layer of paper rods arranged on a first layer of paper rods. The centres of the paper rods of adjacent paper rod layers can, with regard to the profile cross-section, be arranged one above the other or an offset of these centres can be planned.

Within an embodiment of the paper profile with one or several layers of paper rods (paper rod grid, paper rod bond, paper rod framework), grooves may be provided on the surface of the profile. The grooves can improve the haptics of the profile; they can also be a design feature, for example a distinguishing feature, in order to distinguish the profile according to the invention visually and/or haptically from other profiles.

If the profile should have a smooth, i.e. essentially groove-free, surface, the profile may be machined to remove any grooves. The grooves may be filled or the profile may be smoothed by pressing and/or grinding and/or cutting.

On at least one of the long sides of the profile and/or on at least one of the narrow sides of the profile (in sections), at least one curvature and/or slope/bevel can be provided, in particular in such a way that the paper profile has a contour. The contour can be formed ensuring the profile width varies along the profile length. The profile can preferably have the contour of a paddle. On the one hand, this facilitates profile handling, as the profile is wider on one end or on both ends. On the other hand, the fact that the profile is narrower at at least one point saves material, which in turn accelerates biological degradation.

According to a preferred paper profile embodiment, the paper rods may have an identical or almost identical diameter. The paper rods of the paper profile may be made of paper rods of a first diameter and at least of paper rods of a second diameter, with the first diameter being smaller than the second diameter. For example, within a paper rod layer, paper rods with a large (small) diameter may be adjacent to paper rods with a small (large) diameter. If a second layer is intended, the paper rods with the large diameter of the first layer may be adjacent to the paper rods with the small diameter of the second layer. This arrangement results in tight packaging in which the volume of the spaces between adjacent paper rods within the profile is as small as possible. Alternatively, more than two different diameters can be intended, such as a first diameter, a second diameter, a third diameter, a fourth diameter, etc.

Within a paper rod layer, paper rods with the second (larger) diameter can be processed by pressing or flattening so that the variation of the thickness of the layer along the layer width is as small as possible. This makes the layer flatter and less profiled.

It may be useful if at least one paper rod differs from at least one other paper rod in one property, with the property possibly including shape, curvature, colour, surface finish, material and/or flexural rigidity. A profile can thus be provided that is formed from two, three, four or several paper rods, which each differ in colour. The profile therefore becomes multi-coloured without the profile or at least one profile section having to be coloured after production using paper rods. The user or buyer of the profile may also determine which colours the rods should have and which colour design the profile should have.

With regard to the shape, for example, thinner rods can be arranged within a layer on the outside than on the inside, so that the profile is thicker on the inside than on the outside. Some of the paper rods of the paper profile can be rounded at the end or lengthwise. This can result in a paddle shape or the shape of a double paddle. Moreover, some or all of the rods of a profile are pre-treated by lacing, cutting and/or punching, which gives the profile certain characteristics in terms of shape and stability. Individual or several rods may also demonstrate a rough or roughened paper surface. Rods made of different types of paper may also be processed.

To ensure the (essentially solid) paper rods can be arranged in a stable and firm manner within a paper profile, optionally while generating pretension, at least some of the paper rods of the paper profile, preferably all the paper rods of the paper profile in sections, may be connected to one another, in particular, through bonding/adhesion/glueing. Water can be used as an adhesion promoter and/or an adhesive/glue which is particularly suitable for use with foodstuffs. There may be an (adhesive) joint along the long side of the paper rods or a joint at one or more connection points. The connection point can be at the end of the rod or in the middle of the rod. In case of several connection points, they may be distributed roughly along the longitudinal direction of the rod. Alternatively or cumulatively, the paper rods are interconnected along the circumference of the paper profile by at least one shell element formed, in particular, from paper. This shell element can be formed as a paper sleeve; the paper sleeve can be formed in one or more layers. A (paper) shell ensures that the profile has a mainly smooth surface on the outside. The shell element can also consist of several parts, such as several shell sections, which are arranged adjacent to each other along the length of the profile, if necessary with interruptions. The paper profile and/or shell element may include a moisture barrier which is, in particular, compatible with foodstuffs and formed through coating or impregnation, for example. This prevents moisture from penetrating the profile components and therefore increases the longevity of the profile's flexural rigidity.

A marking area for a mark and/or a logo may also be arranged on the profile. The marking area can be provided on a paper rod, on several (adjacent) paper rods or on a shell element arranged around the paper rods. A company or food law notice, a usage notice and/or another notice, such as a label, can be arranged in the marking area.

Technical arrangements to eliminate the disadvantages of the wood-based material, in particular from an environmental point of view, while avoiding the use of plastics also result from a procedure according to claim 10 for the production of a paper profile from paper rods, in particular a paper profile described here. According to this, the paper rod(s) is/are arranged first. In a further procedural step, the paper rod(s) is/are formed and/or joined together. Forming may include pressing, in particular flat pressing. Joining may include adhesion, glueing and/or sealing. Coating with one or more coating agents may also be intended. A further procedural step may involve at least one or more, preferably all, paper rods being processed, in particular through cutting, punching, cutting to length, dyeing, printing, wrapping, smoothing, forming, rounding, flavouring, impregnating and/or cutting. The paper rods may/can be formed from pulp, i.e. a paper material is formed from the pulp. The pulp can be obtained in an environmental sustainable way from down wood, i.e. not necessarily from grown wood, as would be the case with a wood profile.

Further technical arrangements to eliminate the disadvantages of the wood-based material, especially from an environmental point of view, while avoiding the use of plastics result from the use of a paper rod or paper rod composite according to claim 11. The use relates in particular to a paper profile described here, which can be formed according to a procedure described here. According to this, the paper profile or the paper rod or a paper rod composite, i.e. a composite of several paper rods, is used as packaging material and/or packaging element according to the invention, which in this case is of separate inventive significance. The packaging material, packaging element or the packaging equipment component is particularly suitable for food packaging. Since paper is easily biodegradable, there is no need for time-consuming recycling of the packaging component. The packaging element can be a tool for removing the contents of the packaging, a kind of consuming tool as an adjunct to the packaging (picker, handle element). But it can also be used as a mechanical reinforcement component for paper, paperboard or cardboard packaging. The packaging may also serve as a fixing aid and/or reinforcement, for example to reinforce the packaging or to fix the packaging contents inside the packaging.

Particularly preferred is the use of the profile described here as a handle element or stick for confectionery, especially for ice cream. The special feature of "ice lollies" is, e.g., that the foodstuff comes into direct contact with the stick: The ice cream stick is worked into the ice cream and the part of the stick that protrudes from the ice cream serves as a handle for the convenient consumption of the ice cream. By forming this ice cream stick from the paper profile described here, the disadvantages of wooden ice cream sticks are overcome. In case of high mechanical stress, the paper profile ice cream stick according to the invention will not break or tear and will not splinter, especially when bent. If it bends as a result of high mechanical stress, the kink will be significantly less or not sharp-edged at all than would be the case with a break or kink in a wood-based or plastic material. With regard to disposal, the advantages of paper material have already been pointed out. An ice cream stick as described here made of a paper profile described here can be uniformly disposed of as paper waste, for example together with the outer paper packaging of the ice cream. Waste separation into paper waste (outer packaging) and residual waste (stick, e.g. made of wood or plastic) is not necessary. With regard to stability, the ice cream stick described here made from a paper profile described here has a sufficiently high strength that is comparable, in particular, with plastic material. The flexural rigidity is higher compared to conventional materials. The stick according to the invention is able to hold the ice cream and tolerates robust handling by the user/consumer who uses the ice cream stick to eat the ice cream.

It is possible to add or incorporate flavours and/or odours to the paper profile that forms the ice cream stick so that the consumer can experience an additional taste and/or odour experience when consuming the ice cream. Flavouring/Impregnation of a plastic stick is not possible and in case of a wooden stick there would be a risk of injury, especially if a child were to try to chew a flavoured/impregnated wooden stick. In connection with a stick made of a paper profile described herein, further organoleptic possibilities can be exploited.

Further technical arrangements to eliminate the disadvantages of the wood-based material, especially from an environmental point of view, while avoiding the use of plastics result from the use of a paper rod or paper rod composite described here according to claim 12. According to this, the paper profile is preferably used as a hygiene tool and/or as an examination instrument, in particular a medical one, preferably as a mouth spatula or swab or swab holder, which in itself is of inventive significance. In addition to the advantages described above regarding the reduced risk of injury as a result of a reduced risk of breakage, the paper profile described here can also be enriched as a (paper) spatula with medically relevant active ingredients. Additional hygiene precautions, which go beyond what would be necessary with a wooden spatula, are omitted.

Further technical arrangements to eliminate the disadvantages of the wood-based material, especially from an environmental point of view, while avoiding the use of plastics result from the use according to claim 13. According to this, the paper rod or paper rod composite described herein, in particular the paper profile described herein, is suitable as a spring and/or tensioning element, in particular as a shoe tree. Due to the given flexural rigidity of the profile or paper rod composite, a pretension can be generated in the spring and/or tensioning element without breaking. Moreover, the shoe tree is light weight, inexpensive to manufacture and easy to handle, making it suitable for use as an accessory in shoe packaging or for travel purposes.

Further technical arrangements to eliminate the disadvantages of wood-based material, in particular from an ecological point of view, while avoiding the use of plastics, result from the use of an ice cream stick for ice cream according to claim 14, as a spatula, in particular a mouth spatula, for examinations, in particular medical examinations, according to claim 15 and as a tensioning device, in particular a shoe tensioning device, according to claim 16. Accordingly, the ice cream stick, the spatula and the tensioning device are made of a paper profile described here.

A preferred embodiment of the tensioning device may be suitable for transmitting forces and/or torques to its surroundings. For this purpose, the tensioning device may be flexible under the formation of a restoring force. A first paper profile or a first paper rod can be connected, at least in sections, to at least one further paper profile or one further paper rod, particularly at the end, in such a way that the first paper profile or the first paper rod applies a force, especially a restoring or pretensioning force, to a further, in particular a second, paper profile or a further, in particular a second, paper rod in the unbent and/or bent state of the tensioning device. For example, two paper rods of different lengths can be connected at the ends. The longer of the two connected paper rods is pretensioned through bending. When both paper rods now are bent together, they exert forces on each other, resulting in a restoring force that intends to bring the interconnected paper rods to their initial position. The tensioning device is therefore suitable for permanently exerting a force on an object, in particular on the contents of a packaging, for example a packaged shoe, wherein the contents of the packaging are permanently tensioned or stretched in the packaging.

The components mentioned above as well as the stressed components and the components described in the design examples to be used according to the invention are not subject to any special exceptions with regard to their size, shape, material selection and technical design, so that the selection criteria known in the field of application can be applied without restriction.

Further details, characteristics and advantages of the subject matter of the invention result from the subclaims as well as from the following description and the associated drawing, in which design examples of a paper profile are—exemplarily—presented. Individual features of the claims or design shapes may also be combined with other features of other claims and design shapes.

BRIEF DESCRIPTION OF THE FIGURES

In the drawing

FIGS. 5a to 5d show schematic representations of paper profiles, each comprising several layers with several paper rods each, each in lateral view.

DETAILED DESCRIPTION OF EXAMPLES

Figure 1:
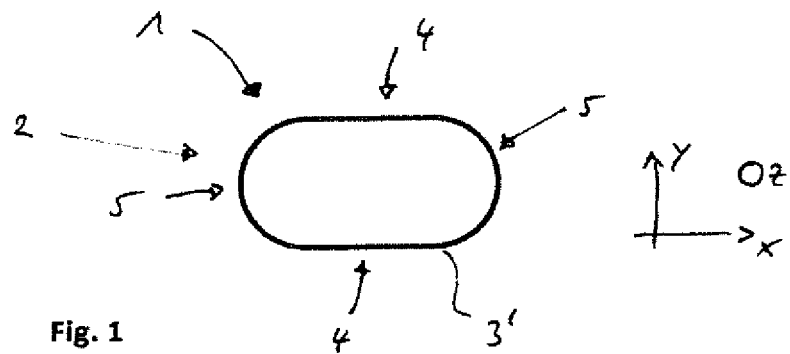
FIG. 1 shows a schematic representation of a paper profile comprising a mechanically formed paper rod in lateral view.

FIGS. 1 to 22b show schematic representations. A paper profile 1 in lateral view can be taken from FIG. 1. FIG. 1 shows the narrow side 2 of paper profile 1. Paper profile 1 according to FIG. 1 is formed from a solid paper rod 3', which is compressed or flattened at two opposite longitudinal positions 4 of an otherwise cylindrically shaped rod 3'. Each of the paper rods shown in the figures can, for example, be formed from a paper web, for example through winding. Adjacent to the longitudinal points 4 of the paper profile or rod are round areas 5, which originate from the originally cylindrical shape of paper rod 3'. Paper profile 1 according to FIG. 1 has a higher flexural rigidity along the axis imagined through the round areas 5 (according to FIG. 1 the y axis) than in the axis running perpendicular to it (according to FIG. 1 the x axis). Overall, this results in a higher flexural rigidity in at least one bending direction than with the cylindrical paper rod from which the paper profile according to FIG. 1 is formed.

For example, paper profile 1 as shown in FIG. 1 can be cut to length from about 76 mm to about 113 mm and then used as ice cream stick 6 for ice cream 7. An ice cream stick 6 formed from profile 1 according to FIG. 1 does not break or tear even under strong mechanical stress and therefore does not splinter. This prevents splinters getting into ice cream 7 or into the ice cream packaging.

Paper profile 1 according to FIG. 1 can have a width of approx. 10 mm. The thickness of profile 1 can be less than 10 mm.

Figure 1A:
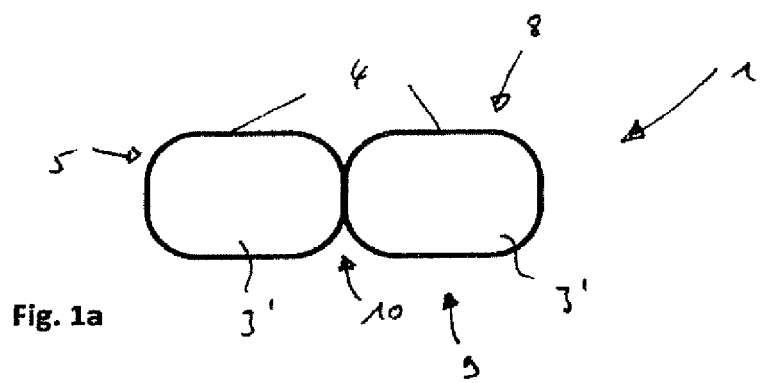
FIG. 1a to 1c show schematic representations of paper profiles, each comprising several mechanically formed paper rods, each in lateral view.
Figure 1B:
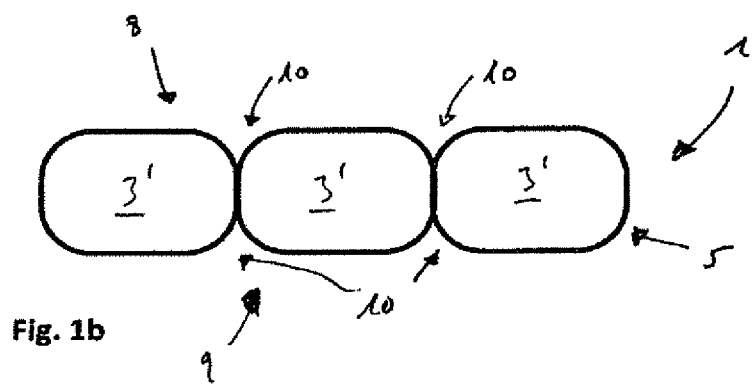
Figure 1C:
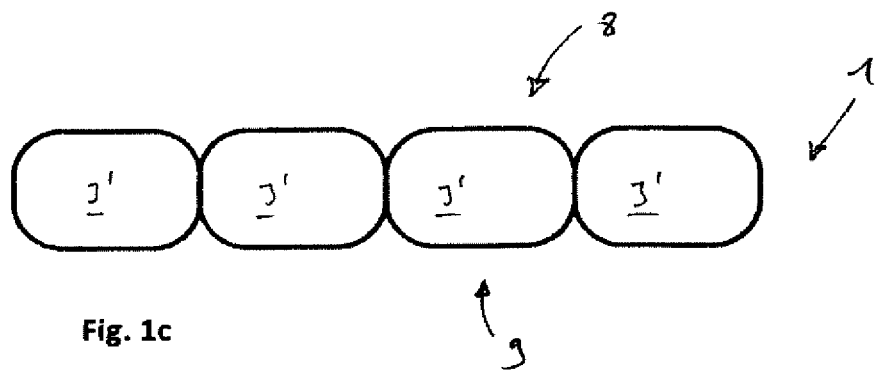

FIGS. 1a to 1c show schematic representations of types of a profile 1, which is made from flat pressed paper rods 3'. A profile 1 comprising two paper rods 3' can be taken from FIG. 1a; according to FIG. 1b three paper rods 3' are provided per profile 1 and according to FIG. 1c there are four paper rods 3' per profile 1. Paper rods 3' are arranged according to FIGS. 1a, 1b and 1c next to each other in one plane. This results in a flat profile 1, wherein the width of the narrow side 2 of profile 1 can be determined by the number of paper rods 3' processed. Paper rods 3' according to FIGS. 1a to 1c may have been flattened through pressing before or after being arranged. It may be helpful to first arrange several paper rods parallel and adjacent to each other, to glue them together if necessary, and to then flatten the paper rod composite formed in this way on at least one side.

As several paper rods 3' are provided, profile 1 as shown in FIGS. 1a, 1 b and 1c has a greater flexural rigidity in at least one bending direction than a single paper rod 3.

FIGS. 1a, 1b and 1c show that profile 1 has one or more grooves 10 on the opposite sides 8, 9. The grooves 10 run parallel to the longitudinal direction of profile 1 and change haptics of profile 1. At the same time, the grooves 10 are suitable for distinguishing profile 1 from other profiles, i.e. as a recognition feature. Finally, when profile 1 is used as a packaging element or packaging instrument, the grooves 10 may be better suited for gripping the product to be packaged, for example a food product such as ice cream. If, for example, profile 1 is used for an ice cream stick, the ice cream will adhere better, in particular longer, to profile 1, which includes the grooves 10; a fact which a user (consumer) will appreciate in that the ice cream will not, or is at least less likely to, detach from the stick in an undesirable way and fall off.

Figure 2A:
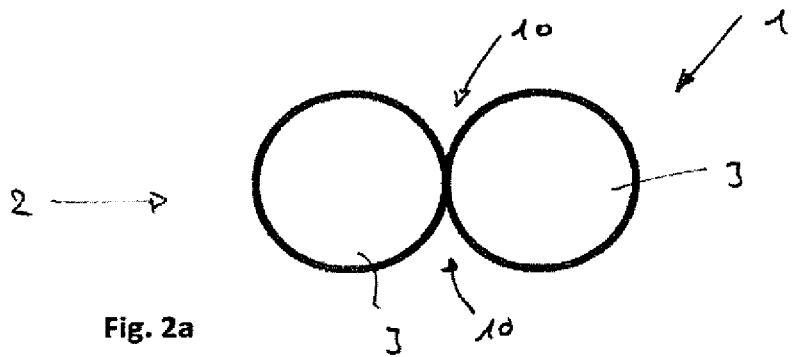
FIGS. 2a to 2c show schematic representations of paper profiles, each comprising several paper rods, each in lateral view.
Figure 2B:
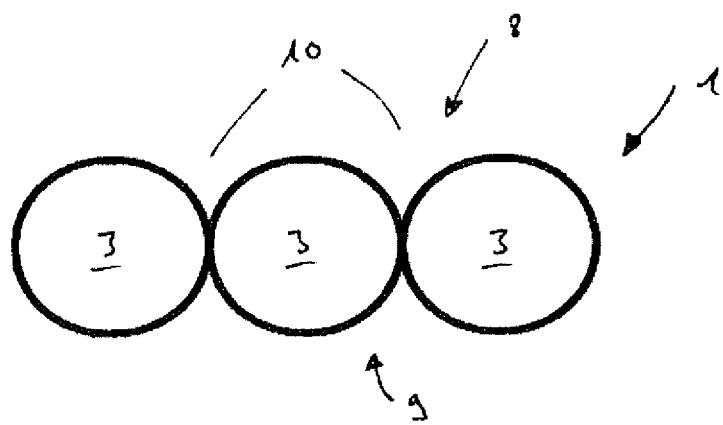
Figure 2C:
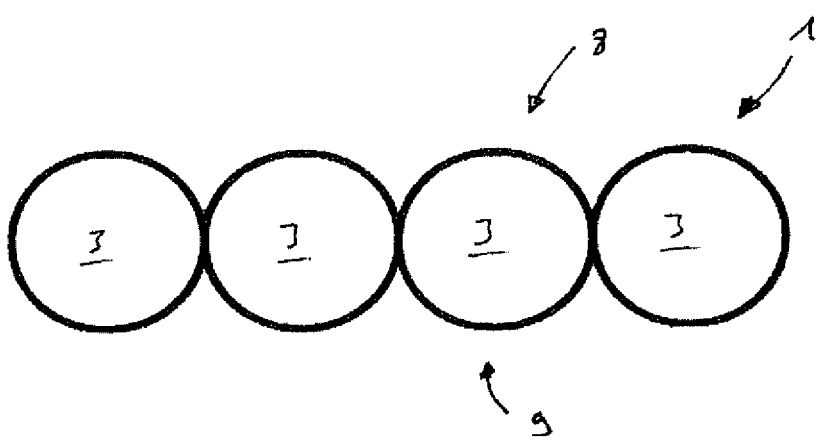

FIGS. 2a to 2c show a paper profile 1, which is formed from several, namely from two, three or four, paper rods 3. The paper rods 3 each have a (circular) round or almost (circular) round cross-section, so unlike in FIGS. 1a to 1c they are not flattened according to FIGS. 2a to 2c. The paper rods 3 according to the profiles 1 shown in FIGS. 2a to 2c can be joined together by glueing, i.e. with adhesive, glue or bonding agent. A different joint may also be provided, for example by using thermal or mechanical means. One groove 10 (FIG. 2a) or several grooves 10 (FIGS. 2b and 2c) are arranged in the area of the contact points 11 of the rods 3. For the grooves 10, the same applies as described above.

Figure 3A:
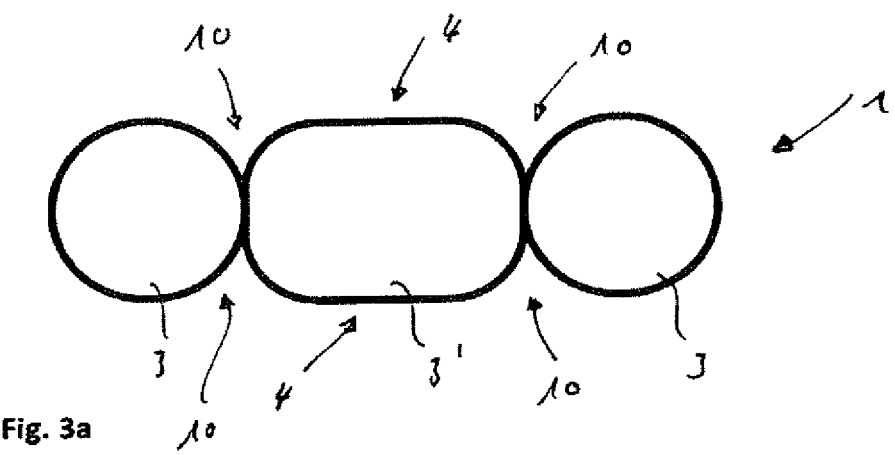
FIG. 3a, 3b show schematic representations of paper profiles, each comprising several paper rods, partially mechanically formed, each in lateral view.
Figure 3B:
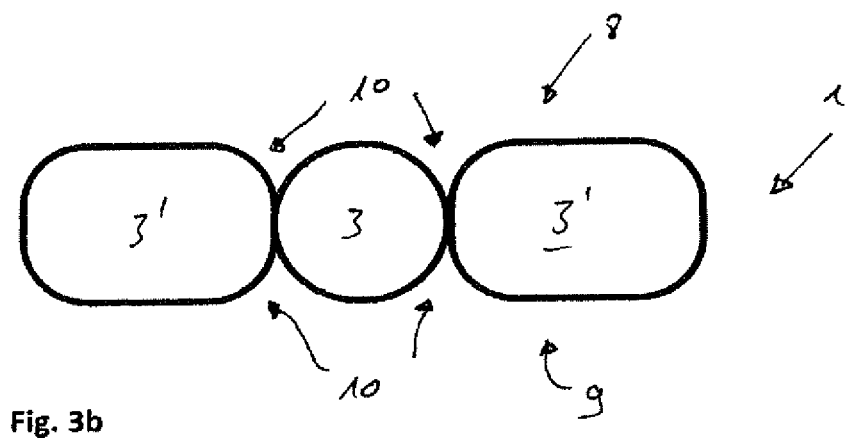

FIGS. 3a and 3b each schematically show a profile 1, which is formed from three paper rods 3, 3' each. The paper rods 3, 3' are arranged in one plane next and parallel to each other. The paper rods 3, 3' of one of the profiles 1 according to FIGS. 3a and 3b differ in their shape. According to FIG. 3a, profile 1 comprises two round or almost round rods 3, between which another flat-pressed rod 3' is arranged. Rod 3' can be flat-pressed before or after arranging the three rods 3, 3' that form profile 1.

According to FIG. 3b, the middle rod 3 is round or almost round, i.e. not flat-pressed, while the outer rods 3' are flat-pressed. With regard to the production of profile 1 according to FIG. 3a or 3b, it may be useful to alternately arrange round or almost round rods with a large diameter (rod 3') and a small diameter (rod 3) next to each other and then press this arrangement flat so that the thickness of profile 1 corresponds approximately to the smaller diameter of the rods involved, i.e. the diameter of the round rods 3.

FIGS. 4a to 4d, 5a to 5d, 6b to 6d and 7 show different variants of profiles 1, each of which is formed in several layers, i.e. where a first layer of 12 paper rods 3 is provided and at least one second paper rod layer 12' is arranged on top. Three, four or more layers (12", . . . ) can also be provided. The multilayer arrangement of paper rods 3 further improves the flexural rigidity of profile 1. Structural changes between the layers (12, 12', 12") can occur, especially when profile 1 is subjected to high bending loads. This means that the paper rods themselves are subjected to less stress and a crack or fracture of profile 1 cannot occur so quickly.

Figure 4A:
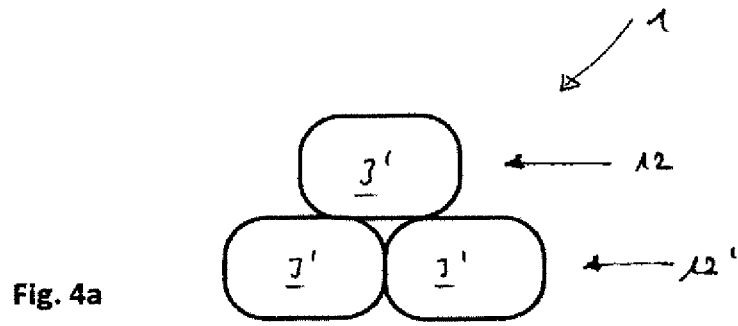
FIGS. 4a to 4d show schematic representations of paper profiles, each comprising several layers with several flattened paper rods, each in lateral view.

FIG. 4a shows a two-layer profile 1 with a first layer 12 formed from two flattened paper rods 3. On the first layer 12 a second layer 12' is arranged, which is formed from a flattened paper rod 3. A profile variant with a similar stack configuration but with round, i.e. not flattened, paper rods 3 instead of flattened rods 3' is shown in FIG. 5a.

Figure 4B:
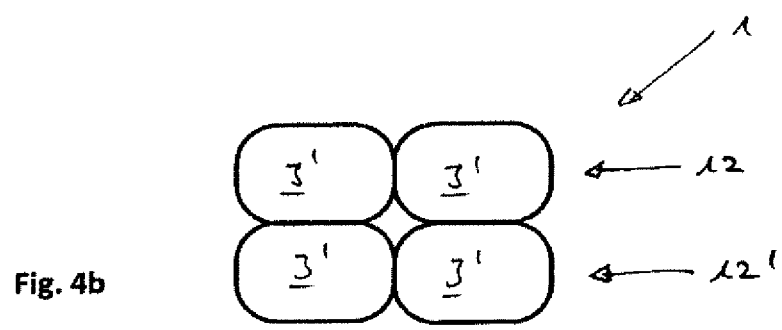
Figure 4C:
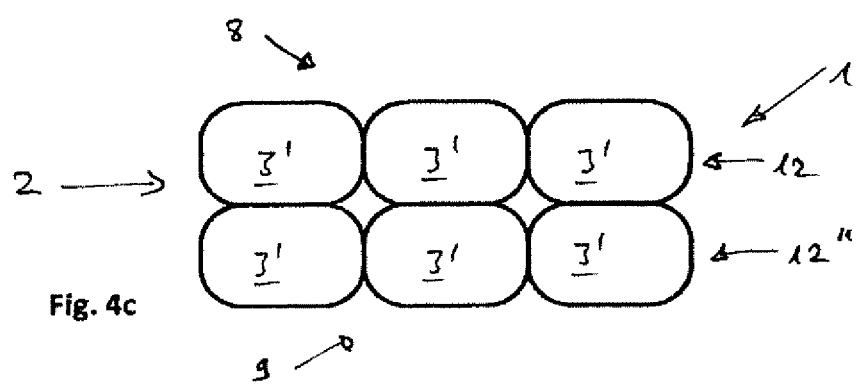
Figure 4D:
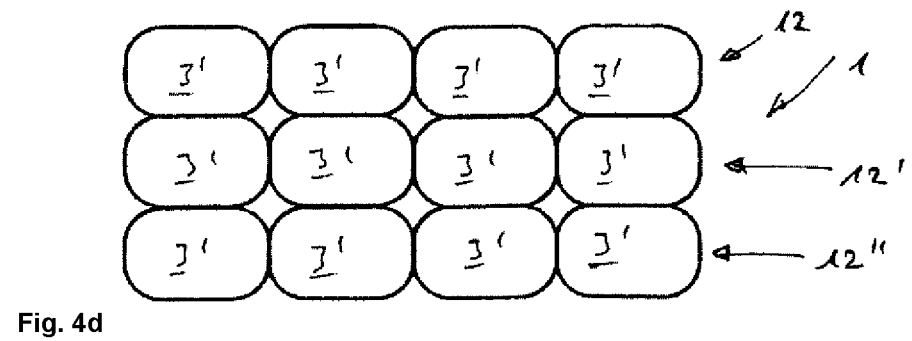

FIGS. 4b and 5b show profile variants in which the first and second layers (12, 12') are each formed from two paper rods. According to FIGS. 4c and 5c each layer 12, 12' comprises three paper rods and according to FIGS. 4d and 5d four paper rods are intended per layer. Further variants that comprise more than four rods per layer (12, 12', . . . ) may be provided. Further profile variants that include more than two paper rod layers, wherein each layer (12, 12', 12", . . . ) may comprise any number of rods 3, 3', may also be provided. In this respect, numerous stack configurations in numerous profile types are possible. By varying the number of layers and/or the number of rods per layer, the following profile properties can be influenced: the profile width (number of rods per layer), the profile thickness (number of layers) as well as the mechanical, in particular bending mechanical, properties of the profile (number of layers and/or rods). By varying the number of layers/rods, profile 1 can thus be adapted to the requirements placed on profile 1. If, for example, an ice cream stick 6 is to be formed from profile 1, a few layers (12, 12') and a few rods 3 per layer can be sufficient (for example one or two layers with up to five rods each). If, on the other hand, a rigid tensioning device, such as a shoe tree, is to be formed from profile 1, a larger number of layers and/or rods per layer would be advisable (for example five to ten layers with five to ten rods each).

Figure 6B:
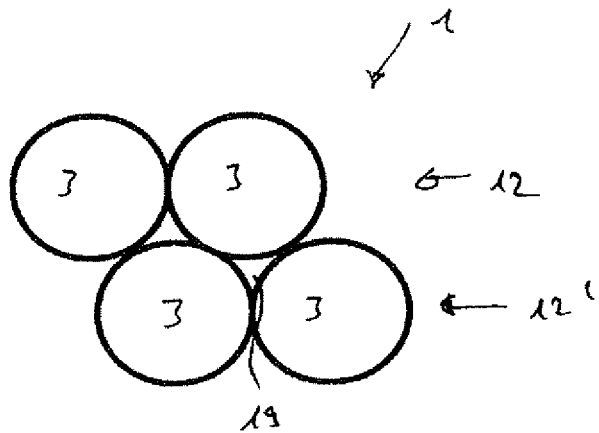
FIGS. 6b to 6d show schematic representations of paper profiles, each comprising several layers offset to each other with one or several paper rods, each in lateral view.
Figure 6C:
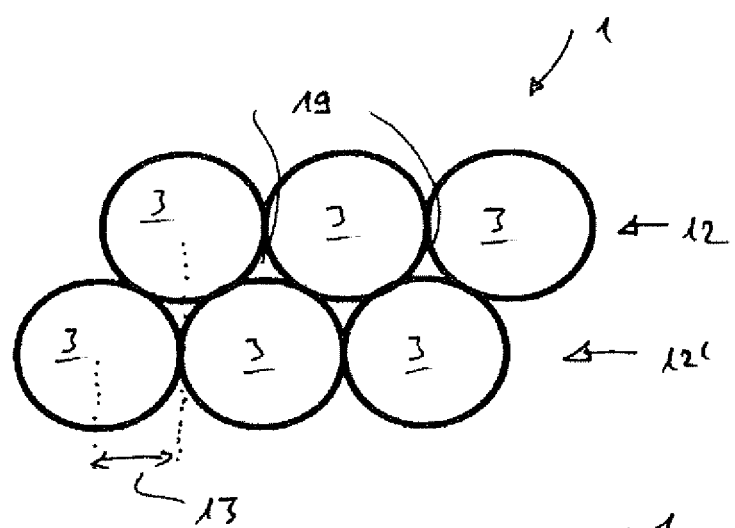
Figure 6D:
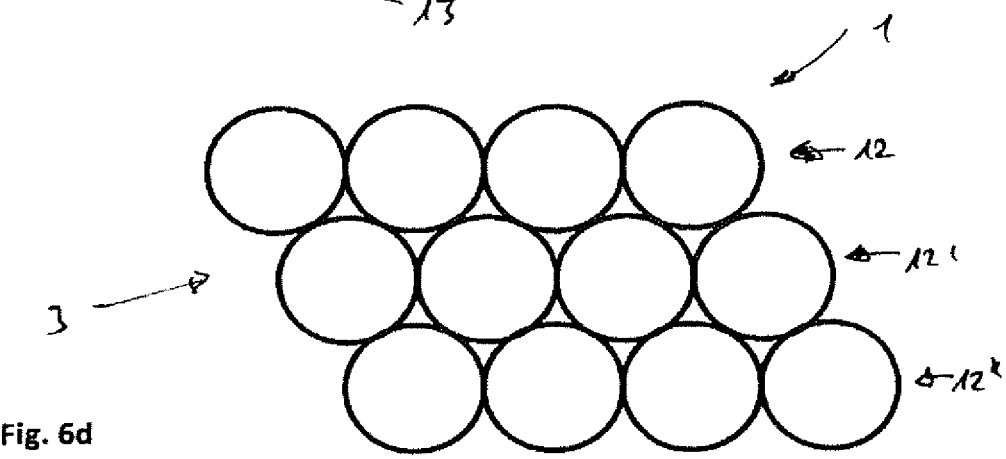

FIGS. 6b to 6d show profile types in which the rods of the second layer 12' are arranged in the groove 10 or in the grooves 10 between the rods 3 of the first layer 12. In this respect, the stack configurations according to FIGS. 6b to 6d include a lateral offset 13 of adjacent layers. In line with the stack configurations (shown here as an example) according to FIGS. 6b to 6d, the volume of the spaces 19 between the rods 3, 3' is reduced, wherein a higher density and stability of profile 1 can be achieved. In the case of a high strength requirement, the stack configuration according to FIGS. 6b to 6d is to be preferred; in the case of a high bending strength, the profile configurations according to FIGS. 4a to 4d and 5a to 5d respectively could be preferred.

Figure 7:
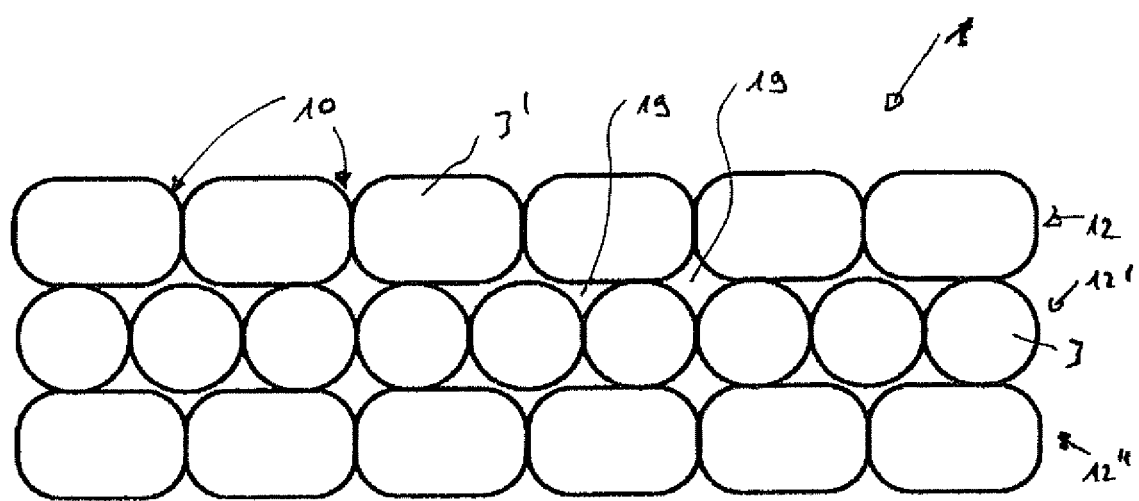
FIG. 7 shows a schematic representation of a paper profile comprising several layers of partially flattened paper rods, in lateral view.
Figure 8A:
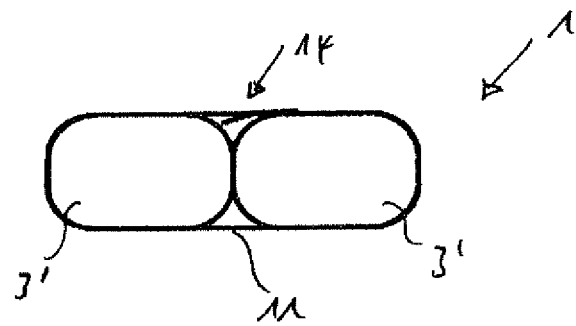
FIGS. 8a to 8c show schematic representations of paper profiles, each comprising a wrapped layer with several flattened paper rods, each in lateral view.
Figure 8B:
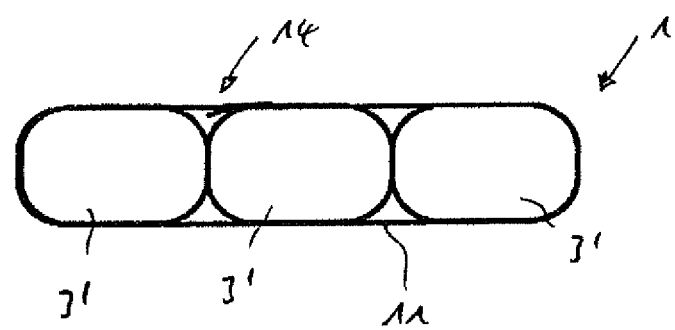
Figure 8C:
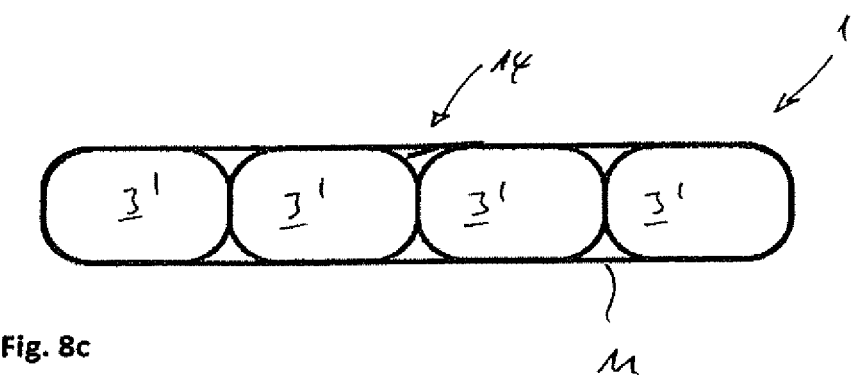
Figure 9A:
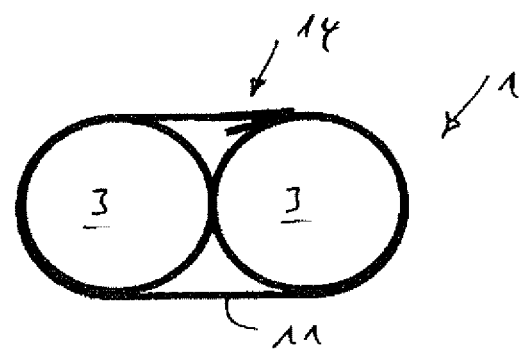
FIGS. 9a to 9c show schematic representations of paper profiles, each comprising a wrapped layer with several paper rods, each in lateral view.
Figure 9B:
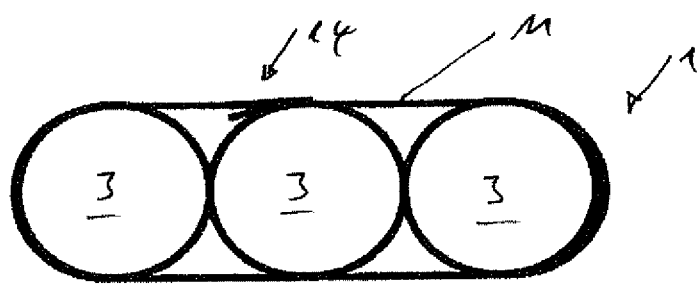
Figure 9C:
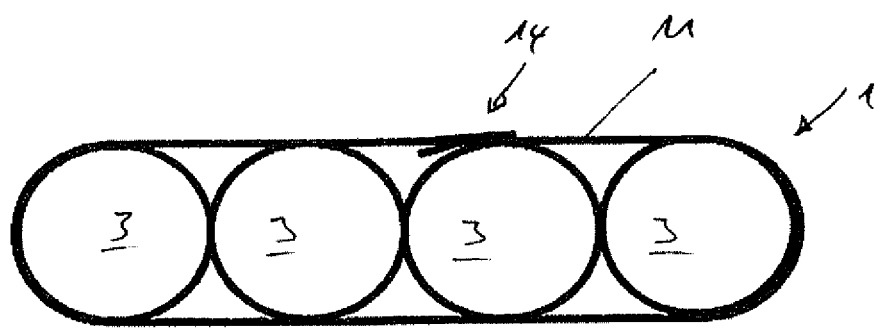
Figure 10A:
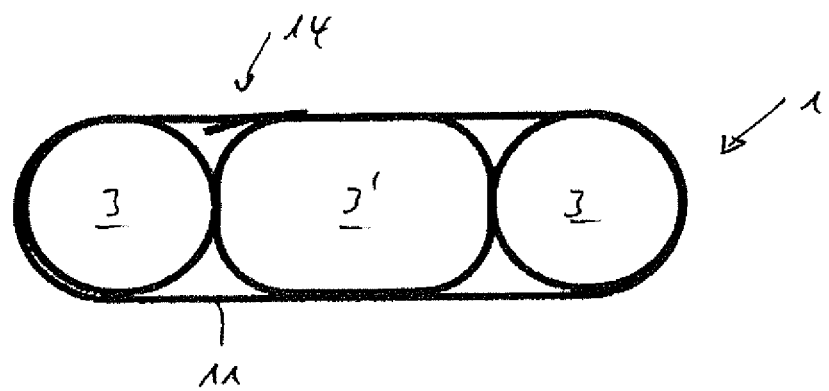
FIG. 10a, 10b show schematic representations of paper profiles, each comprising a wrapped layer with several, partly flattened, paper rods, each in lateral view.
Figure 10B:
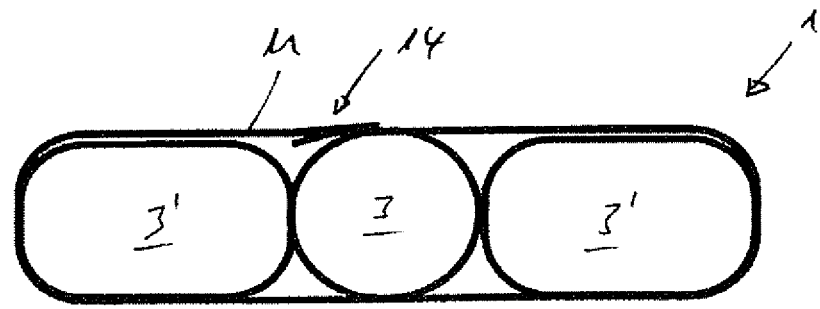
Figure 11A:
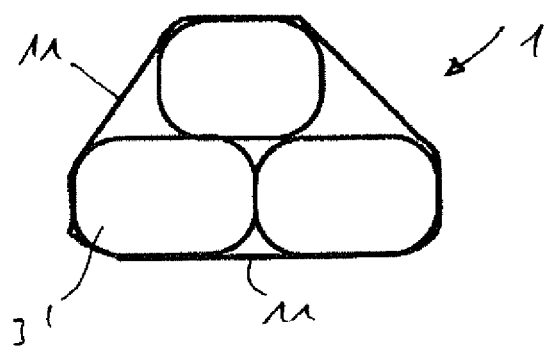
FIG. 11a to 11d show schematic representations of paper profiles, each comprising several wrapped layers each with one or more flattened paper rods, each in lateral view.
Figure 11B:
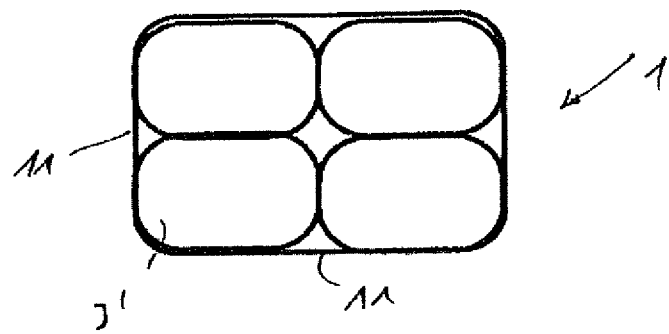
Figure 11C:
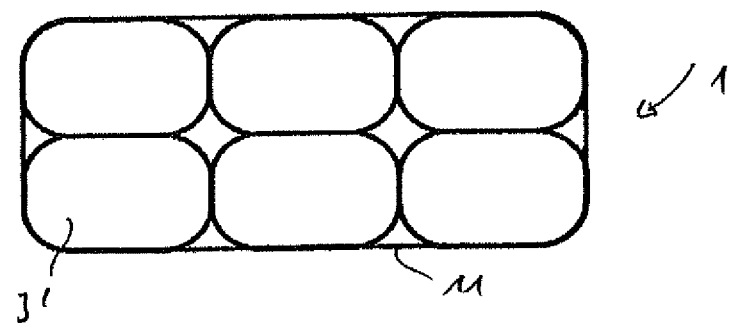
Figure 11D:
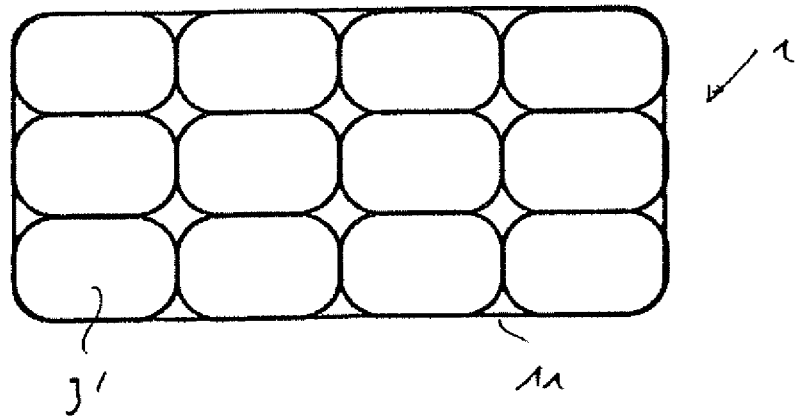
Figure 12A:
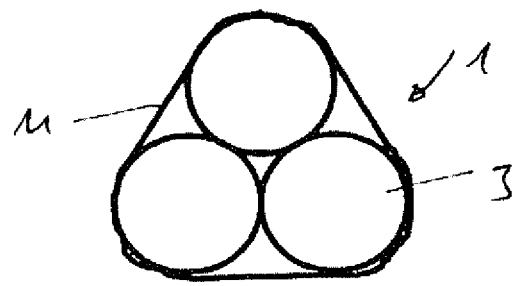
FIGS. 12a to 12d show schematic representations of paper profiles, each comprising several wrapped layers each with one or more paper rods, each in lateral view.
Figure 12B:
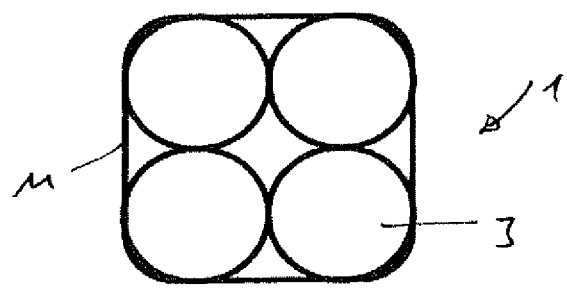
Figure 12C:
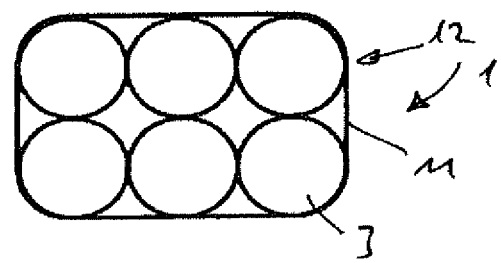
Figure 12D:
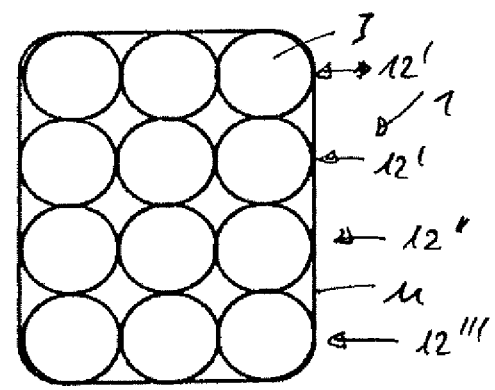
Figure 13A:
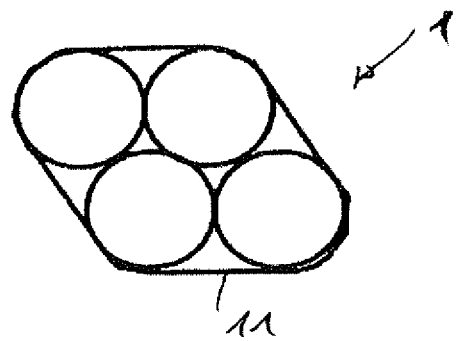
FIGS. 13a to 13c show schematic representations of paper profiles, each comprising several wrapped and offset layers each with several paper rods, each in lateral view.
Figure 13B:
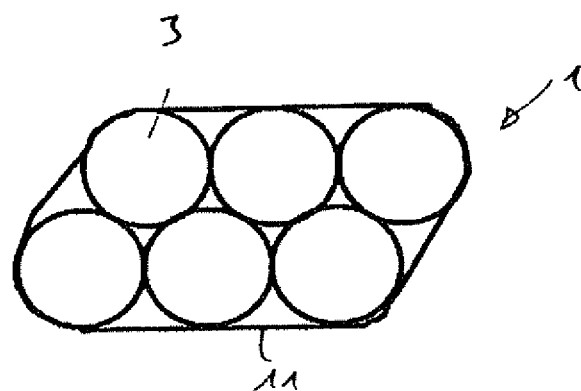
Figure 13C:
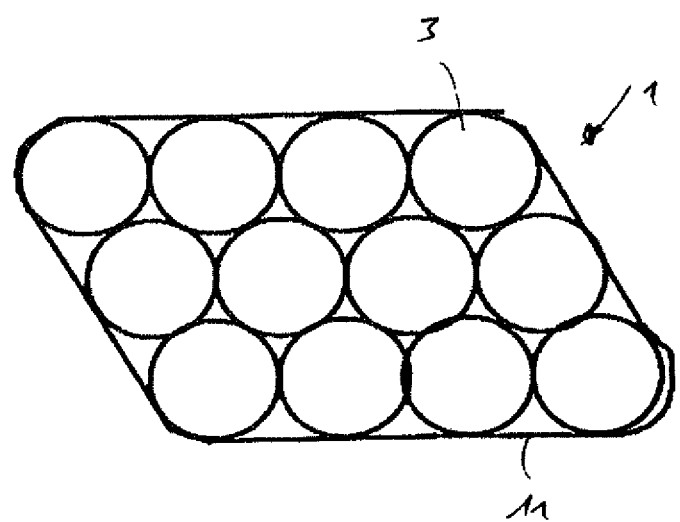

A profile configuration with three layers 12, 12', 12" and comprising rods 3 with a first diameter and flattened rods 3' can be taken from FIG. 7. The flattened rods 3' are formed from originally round rods through flat pressing, whereat the originally round rods have a second diameter which was larger than the first diameter of the round rods 3'. According to FIG. 7, the middle layer (12') is formed from round rods 3, the adjacent outer layers (12, 12") are formed from flat pressed rods 3'. Alternatively, a type can be provided in which the round rods 3 form the outer layers and the flattened rods the middle layer. For more than three layers, alternating or repeating configurations may be provided (ABABAB, ABBABBABBA, ABBAABBAABBA and many more, where A, B are variables for differently formed layers).

In all configurations according to FIGS. 1a to 1c, 2a to 2c, 3a, 3b, 4a to 4d, 5a to 5d, 6b to 6d and FIG. 7, the rods 3, 3' may be bonded or glued to one another or adhere otherwise to one another and thus form an (adhesive or glue) bond. Alternatively, instead of a bonding agent (adhesive, glue) a shell element 11 may be used which surrounds the (at least outer) rods 3, 3' of profile 1 at least in sections. It is also possible to provide several shell elements 11 which are arranged along the longitudinal direction of profile 1 and which produce a stable connection of the rods (3, 3') of profile 1.

Figure 14:
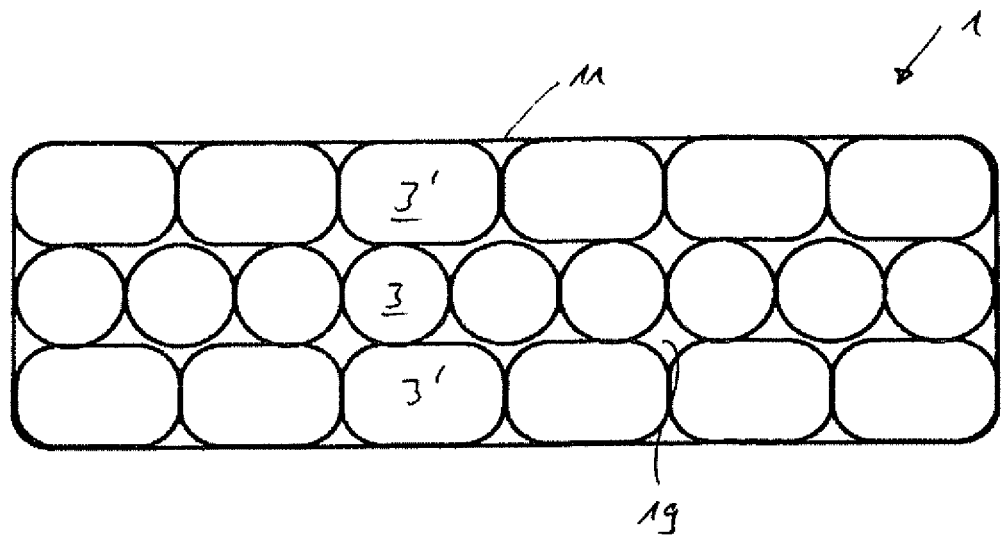
FIG. 14 shows a schematic representation of a paper profile comprising a plurality of wrapped layers each having a plurality of partially flattened paper rods, each in lateral view.

Analogous to the stack configurations of different profile types described above, FIGS. 8a to 8c, 9a to 9c, 10a, 10b, 11a to 11d, 12a to 12d, 13a to 13c as well as FIG. 14 show configurations in which the rods or the outer rods are wrapped with a sleeve 11. The sleeve or shell element 11 may be formed from paper, in particular from a strip of paper wrapped around the rods. The paper shell 11 can be formed from multilayer paper material. The end areas 14 of the shell element 11 can overlap at least in sections, as shown schematically in FIGS. 8a to 8c and 9a to 9c as well as in FIGS. 10a and 10b. The overlapping end areas 14 can be bonded or glued together; a mechanical connection of the end areas 14 can also be provided, such as a fold and/or kink or rebate. A joint of the end areas 14 through thermal energy input, e.g. with a weld seam, can also be provided. The end areas 14 of the shell strip may also abut each other (edge-to-edge arrangement). A connecting element, such as an adhesive strip, may also be used to connect the end areas 14 of the shell 11.

By wrapping the rods 3, 3' with a shell element 11, profile 1 obtains an essentially smooth shell surface. The shell element 11 can be coloured and/or can be printed with a label and/or with an image and/or with a logo, making profile 1 more cost-effective to design. Moreover, the shell element 11 achieves better haptics of profile 1; the user of profile 1 cannot directly recognise the rods 3, 3' and has the impression of holding a compact, stable, light and environmentally friendly paper profile in his/her hands. This property of the profile is particularly desirable when profile 1 is used in conjunction with packaging components or packaging equipment.

Figure 15:
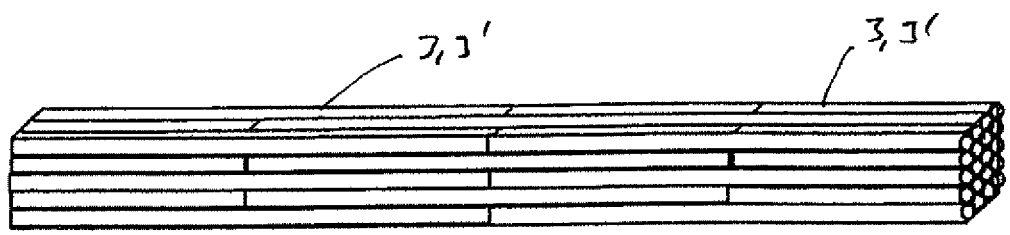
FIG. 15 shows a paper rod composite in perspective view.

A paper rod composite 15 from a large number of arranged paper rods 3 can be taken from FIG. 15. The paper rods 3, 3' are not only arranged next to each other but also behind each other. A profile 1 of any expansion in the z direction (length) can thus be formed. In particular, a profile 1 with a profile length of, e.g., approx. 1 m or longer can be produced and is formed from a large number of rods 3, 3' with a rod length of, e.g., approx. 20 cm or less.

Figure 16A:
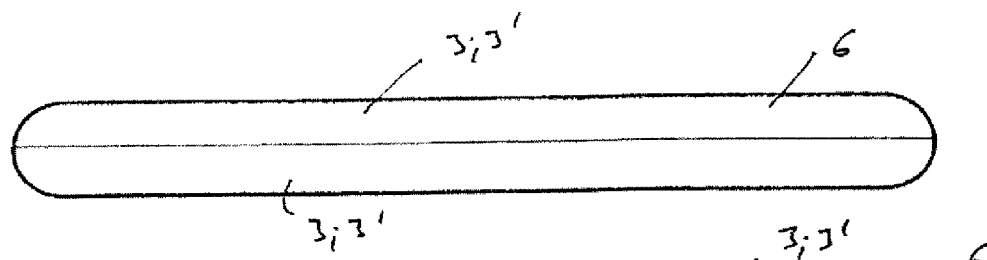
FIGS. 16a to 16c show schematic representations of paper profiles with several paper rods, each in top view.
Figure 16B:
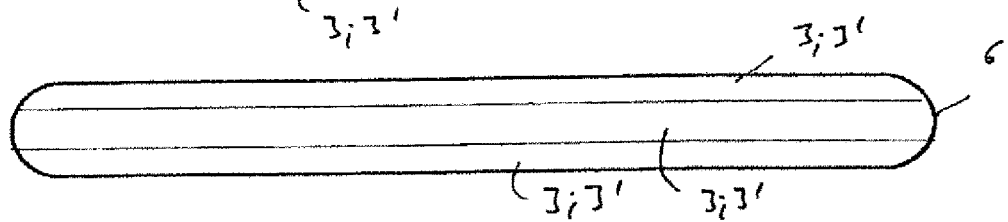
Figure 16C:
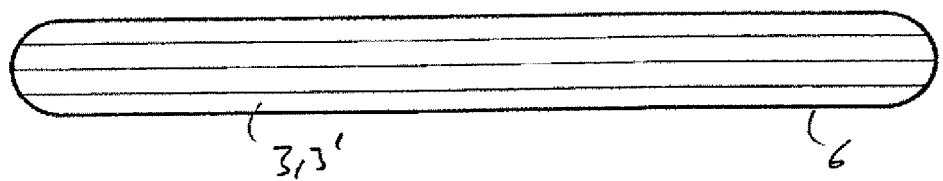

Examples of the use of paper profile 1 described here can be found in FIGS. 16a to 16c, 17, 18a, 18b, 19a, 19b, 20 and 21. FIGS. 16a to 16c each show ice cream sticks 6 for ice cream 7. The ice cream sticks 6 are packaging equipment of an ice cream packaging. Ice cream 7 is arranged on ice cream stick 6. Ice cream with an ice cream stick, i.e. an ice lolly, is arranged in an outer packaging made of paper or cardboard. The consumer usually removes ice cream stick 6 together with ice cream 7 from the outer packaging and eats ice cream 7 while grabbing and holding the ice cream stick. FIG. 6a shows an ice cream stick 6 formed from a paper profile 1, which in turn is formed from at least one paper rod layer 12 with two adjacent paper rods 3, 3'. The paper rods 3, 3' can be round or flattened. The rods 3, 3' can be glued together or wrapped with a shell element 11. Profile 1 is cut to the length of ice cream stick 6, e.g. by cutting or punching, rounded at the ends if necessary or cut accordingly.

According to FIG. 16b, a profile with three rods (3, 3') has been used to make ice cream stick 6; according to FIG. 16c, it is four rods (3, 3'). The profiles 1 for the production of the ice cream sticks 6 according to FIGS. 16a to 16c all have approximately the same profile width, only the width (diameter) of the paper rods (3, 3') varies.

Figure 17:
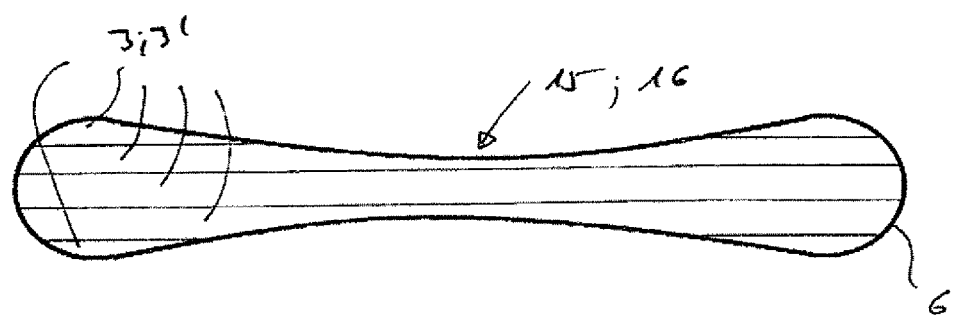
FIG. 17 shows a schematic representation of a paper profile with a contour in top view.

FIG. 17 shows an ice cream stick 6 formed from a profile 1 with a contour 15. Contour 15 can be arranged in profile 1 through cutting or punching. Ice cream stick 6 according to FIG. 17 has a waistline 16 along the longitudinal direction, wherein stick 6 has the shape of a paddle or double paddle. The paddle-shaped stick lies better in the hand, the consumer can hold the ice cream better and safer. At the same time, paper material is saved in the waistline area 16, which offers ecological advantages. In addition, contour 15 makes the stick lighter, which reduces the effort required for transporting and storing large quantities.

Figure 18A:
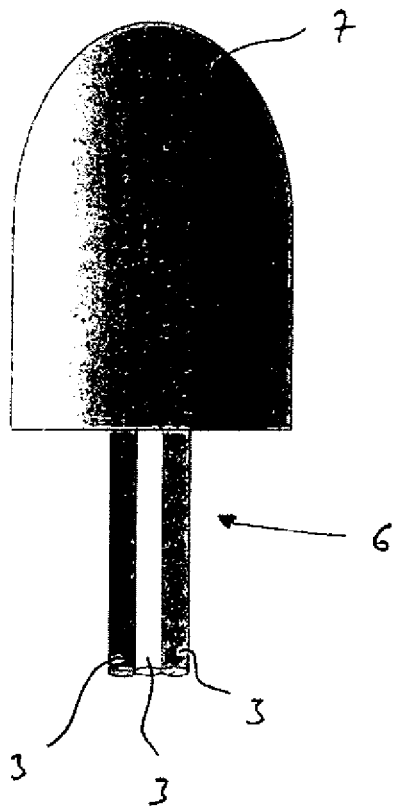
FIG. 18a, 18b shows schematic representations of an ice cream in lateral view.
Figure 18B:
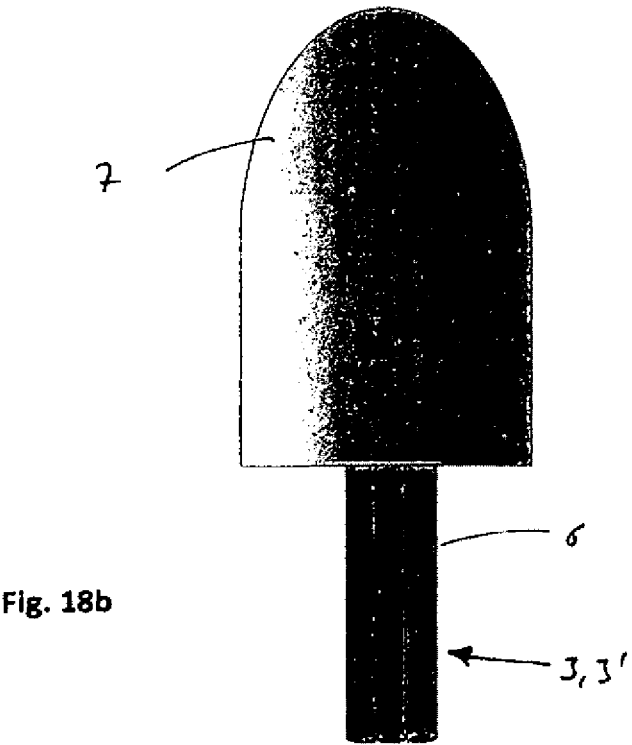
Figure 19A:
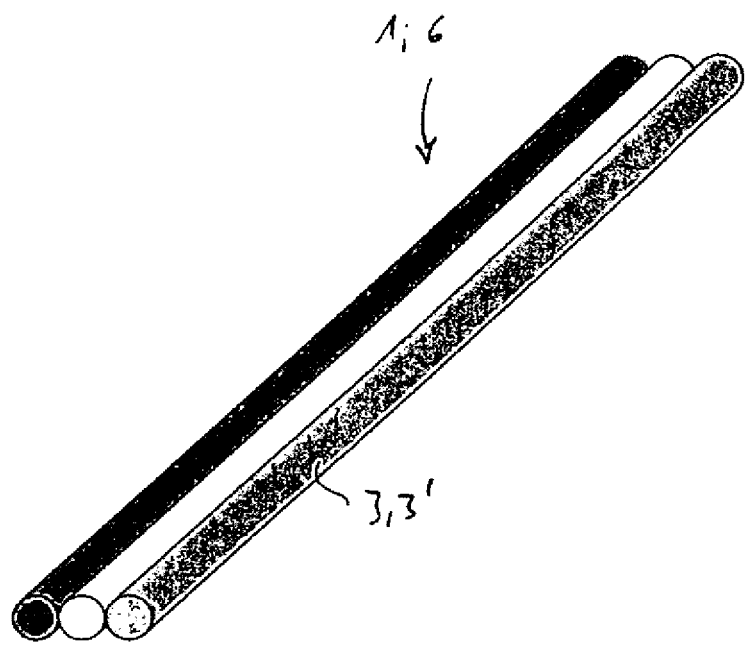
FIG. 19a, 19b shows schematic representations of ice cream sticks in perspective view.
Figure 19B:
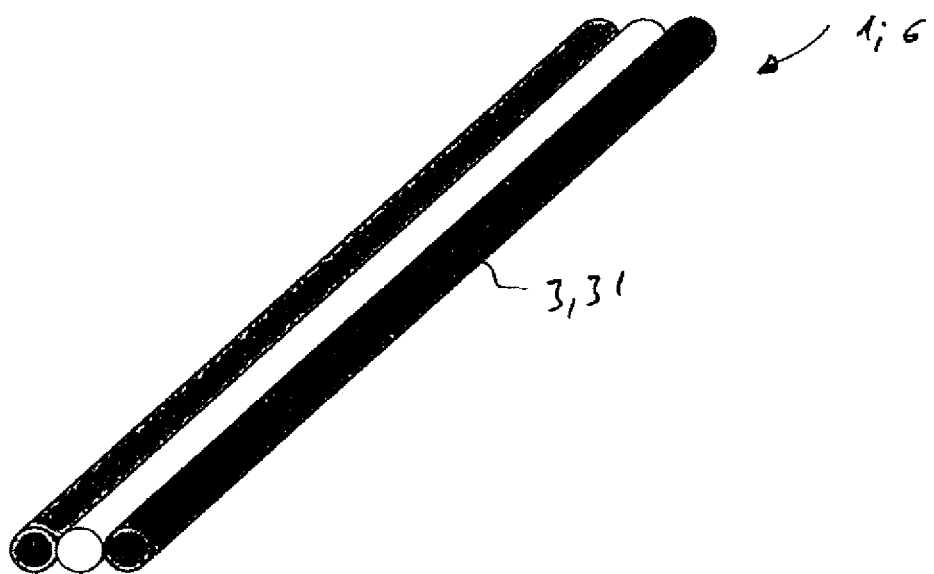
Figure 20:
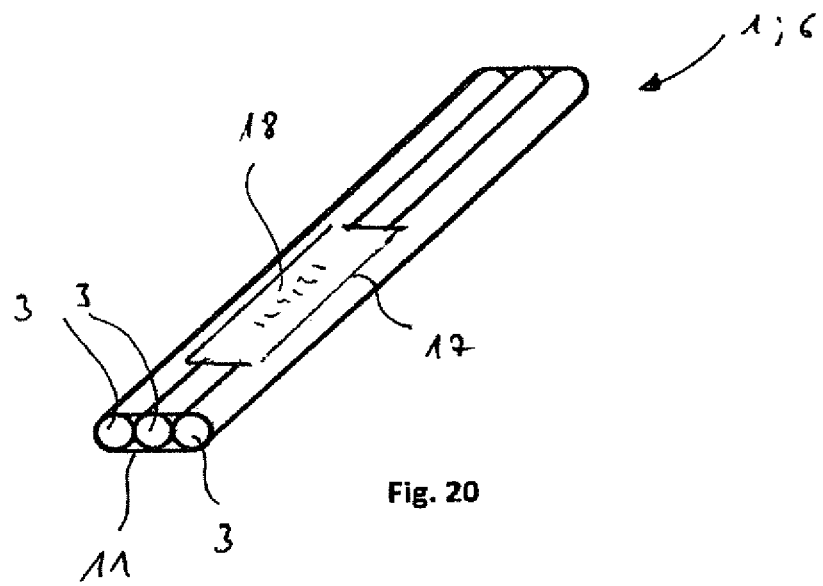
FIG. 20 shows a schematic representation of an ice cream stick in perspective view.
Figure 21:
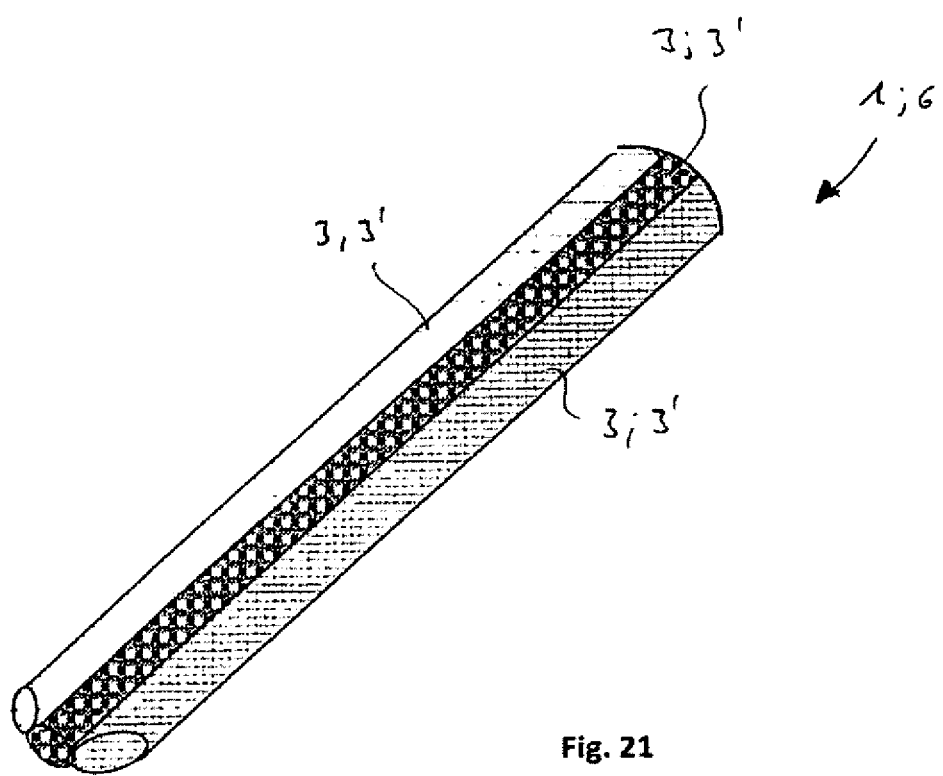
FIG. 21 shows a schematic representation of an ice cream stick variant in perspective view.

An ice cream 7 with ice cream sticks 6 arranged in ice cream 7 can be taken schematically from FIGS. 18a and 18b. Ice cream stick 6 according to FIG. 18b is formed from a profile 1 which comprises three (identically) coloured paper rods 3. Ice cream stick 6 according to FIG. 18a is formed from a profile 1 which comprises three paper rods 3, each of which differs in colour. Thus, the ice cream stick may be made in the colours of the ice cream manufacturer's trade mark or colours may be used which indicate national or regional origin. An ice cream stick 6 with the paper rod colours black, red and yellow, for example, would indicate an ice cream of German origin, an ice cream stick 6 with the colours blue, white and red would indicate an ice cream of French origin or taste and an ice cream stick 6 with the colours green, white and red would indicate Italy as the country of origin. Any number of other colour combinations are possible. A coloured profile 1 is produced by using coloured paper rods 3, 3'. Alternatively, the colour or appearance of the profile can be achieved with a coloured or designed shell 11.

FIGS. 19a, 19b, 20 and 21 show different profile types with different design characteristics. The selection of the 3, 3' paper rods enables many different design variants. A further design measure is the arrangement of a marking area 17 on profile 1. Marking area 17 can be arranged on rods 3, 3' or on a shell element 11. Marking area 17 may be printed or embossed. A label 18 and/or a logo and/or a (picture) image may be arranged in marking area 16.

Figure 22A:
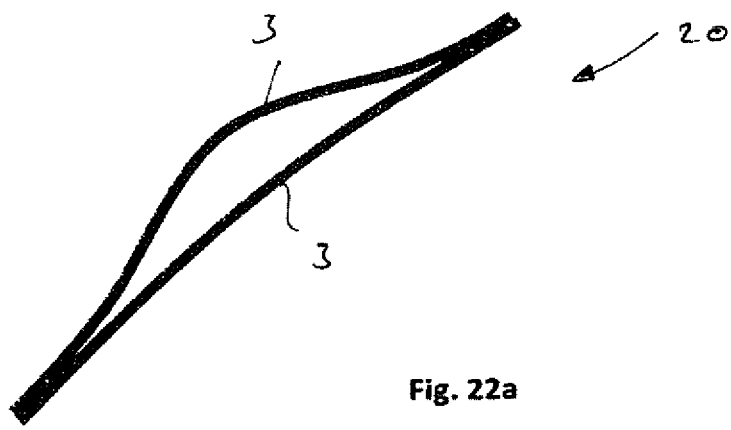
FIG. 22a shows a schematic representation of a tensioning device for a shoe in unbent condition.

A schematic lateral view of a shoe tree 20 can be taken from FIG. 22a. Shoe tree 20 comprises a first paper rod 3 and a second paper rod 3. Both paper rods 3 are interconnected at the ends, wherein the first paper rod 3 is slightly longer than the second paper rod 3. Due to the difference in length of both paper rods 3 and in that a joint of the paper rods 3 is provided at the respective rod ends, the longer rod 3 has a bend, wherein the tensioning device 20 has a mechanical pretension.

Figure 22B:
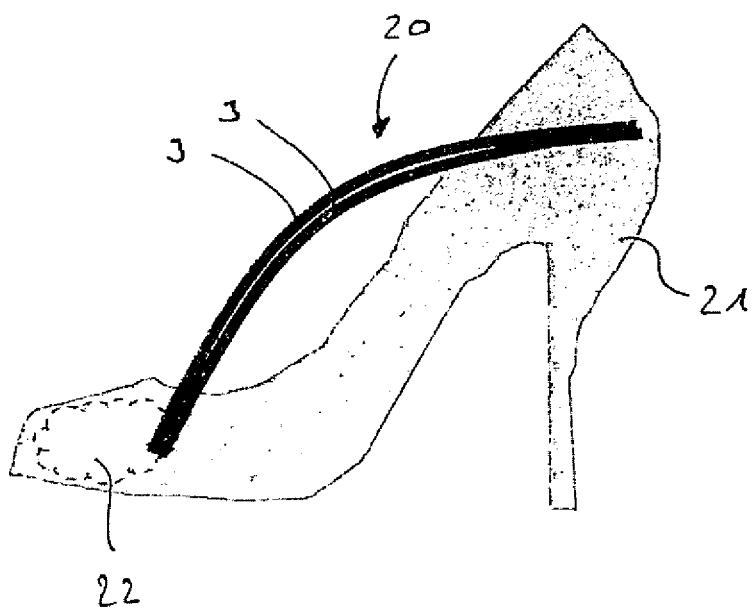
FIG. 22b shows a schematic representation of a bent tensioning device in a lady's shoe.

According to the schematic diagram of FIG. 22b, the shoe tree is used in a woman's shoe 21 according to FIG. 22a. Stuffing paper against which the shoe tree 20 presses has been arranged in the front area of woman's shoe 21. Compared to the unbent starting position shown in FIG. 22a, shoe tree 20 is now mechanically bent, wherein the first and the second paper rod transmit forces to each other. Bending of the paper rods 3 of the tensioner 20 is reversible, i.e. the rods 3 can be returned to their original position (FIG. 22a) without material damage. Due to the pretension (FIG. 22a), the shoe tree "wants" to return to its original shape (FIG. 22a), wherein shoe tree 20 transfers a restoring force to shoe 21 that tensions shoe 21.

Shoe tree 20 according to FIGS. 22a and 22b is made of paper rods, i.e. paper material. Stuffing paper 22 is also made of paper material. If shoe 21 with shoe tree 20 and stuffing paper 22 is now (re)packed in a (shoe) box, the entire shoe packaging (carton+stuffing paper 22+shoe tree 20) can be disposed of in the paper waste bin. Waste separation of the shoe packaging is not necessary, because apart from paper material no other packaging material is necessary.

LIST OF REFERENCE NUMBERS

1 Paper profile
2 Narrow side
3, 3' Paper rod
4 Longitudinal points
5 Round area
6 Ice cream stick
7 Ice cream
8 Side
9 Side
10 Groove
11 Shell element
12, 12', 12" Position
13 Offset
14 End area
15 Contour
16 Waistline
17 Marking area
18 Labelling
19 Space
20 Shoe tree
21 Shoe
22 Stuffing paper

The invention claimed is:

1. A paper profile for use as a packaging element or packaging equipment for food packaging, wherein said paper profile has an elongated shape having at least one long side in longitudinal direction, at least one narrow side in transverse direction, and a profile thickness in a transverse direction, characterised in that the paper profile is formed from two or more paper rods, each of said papers rods have substantially no hollow spaces, each of said paper rods is a flexurally rigid roll prior to being used in said paper profile, wherein the flexural rigidity of the paper profile in at least one bending direction corresponds at least to the flexural rigidity of one of the paper rods, and wherein a restoring force counteracting the bending direction can be generated at least in sections by bending the paper profile, a plurality of said paper rods have a same cross-sectional size and profile along a longitudinal length of said paper rods, a final cross-sectional shape of a plurality of said paper rods is selected from the group consisting of a circular shape, oval shape and stadium shape.

2. The paper profile according to claim 1, characterised in that the flexural rigidity of the paper profile exceeds the flexural rigidity of one of the paper rods in at least one bending direction.

3. The paper profile according to claim 1, characterised in that prior to forming said paper profile at least one of the paper rods is machined through flattening so that at least one side of the paper profile is flat.

4. The paper profile according to claim 1, characterised in that the paper profile is formed A) from at least one layer of said paper rods in which at least two paper rods are arranged next to and parallel to one another, a plurality of the paper rods comprising a curvature and/or slope arranged on at least one long side or on at least one narrow side so that the paper profile has a contour, and/or B) in several layers from paper rods, wherein at least one second layer of paper rods is arranged on a first layer of paper rods.

5. The paper profile according to claim 1, characterised in that a plurality of the paper rods of the paper profile are formed from paper rods with a first diameter and and one or more paper rods with a second diameter, the first diameter is smaller than the second diameter and the paper rods with the second diameter have been machined through flattening to form a flat surface on two sides of the paper rods.

6. The paper profile according to claim 1, characterised in that a plurality of paper rod differs in a property from a plurality of other paper rods, wherein the property is one or more of shape, curvature, colour, surface finish, material and flexural rigidity.

7. The paper profile according to claim 1, characterised in that the paper rods of the paper profile, are connected to one another and/or to one another at least in sections through adhesion or bonding.

8. The paper profile according to claim 1, characterised in that a plurality of the paper rods are connected to one another along the circumference of the paper profile by at least one shell element that is formed from paper, the at least one shell element overlying only a portion of an outer surface of two or more paper rolls.

9. The paper profile according to claim 1, characterised by a marking area which is arranged on the paper profile and on which a marking and/or a logo can be positioned.

10. The paper profile according to claim 1, wherein said paper profile is formed of a plurality of flexurally rigid paper rods, one or more of said paper rods having a cross-sectional shape selected from the group consisting of a circular shape or an oval shape, each of said paper rods formed of a paper web formed by a winding process, each of said paper rod is formed from a layer of wound paper.

11. The paper profile according to claim 1, wherein a diameter of each paper rod is 1-12 mm.

12. The paper profile according to claim 1, wherein each of said paper rods having a flexural rigidity that is at least two times greater than a flexural rigidity of a similarly dimensioned paper or cardboard body not formed/manufactured from a paper web.

13. The paper profile according to claim 1, wherein said paper profile includes a first layer of paper rods positioned side-by-side and parallel to one another, a plurality of said paper rods connected by one or more of a food-grade adhesive, thermal means, and a paper sleeve, said paper profile including a plurality of grooves, each groove is located between two adjacently positioned paper rolls, said plurality of grooves positioned parallel to one another.

14. The paper profile according to claim 1, wherein said paper profile is food-compatible and consists essentially of adhesive and wood pulp and/or cellulose.

15. The paper profile according to claim 1, wherein said paper profile further includes a second layer of paper rods positioned side-by-side and parallel to one another, said second layer positioned beneath said first layer, said paper rods in said first and second layers positioned parallel to one another, a plurality of said grooves positioned between said first and second layers.

16. The paper profile according to claim 1, wherein said paper profile includes a paper sleeve having a food-grade moisture barrier.

17. The paper profile according to claim 1, wherein a plurality of said paper rods have a different longitudinal length.

18. The paper profile according to claim 1, wherein a plurality of said paper rods have a different cross-sectional profile along a longitudinal length of said paper rods.

19. The paper profile according to claim 1, wherein at least one of said paper rods is machined through flattening prior to forming said paper profile so that said paper rod includes a flat profile in at least one side.

20. The paper profile according to claim 1, wherein a plurality of said paper rods have one or more different properties selected from the group consisting of shape, curvature, colour, surface finish, material, and flexural rigidity.

21. The paper profile according to claim 1, wherein said paper profile further includes a marking area on which a marking and/or a logo is positioned.

22. The paper profile according to claim 1, wherein said paper profile further includes flavouring agent and/or odour agent impregnated in one or more of said paper rods and/or said paper sleeve, said flavouring agent and/or odour agent selected to enhance an experience of a consumer when consuming a food product on said paper profile.

23. The paper profile according to claim 1, characterised in that a plurality of the paper rods are at least partially connected together by a shell element, the shell element overlying only a portion of an outer surface of two or more paper rolls.

24. The paper profile according to claim 23, characterized in that the shell element is formed from paper.

25. The paper profile according to claim 23, characterized in that a plurality of the paper rods have a cross-sectional shape selected from the group consisting of a circular shape or an oval shape after the paper profile is fully formed, a plurality of the paper rods is formed of a winding of paper, a plurality of the paper rods is essentially void-free.

26. The paper profile according to claim 25, wherein at least one of said paper rods is machined through flattening so that said paper rod includes a flat profile in at least one side and a curved profile on at least one other side.

27. A paper profile for use as a packaging element or packaging equipment for food packaging, wherein said paper profile has a top, a bottom, a first side, an opposite second side, a first end and an opposite second end, said paper profile having an elongated shape; said paper profile including first, second and third paper rolls, each of said first, second and third paper rolls has substantially no hollow spaces, each of said first, second and third paper rolls is formed of a rolled-up web of paper, said each of said first, second and third paper rolls have substantially no hollow spaces prior to being used in said paper profile, said first, second and third paper rolls have a same cross-sectional size and profile along a longitudinal length of said paper rods, a cross section shape of said first, second and third paper rolls in a final form of said paper profile is selected from the group consisting of a circular shape, oval shape and stadium shape, each of said first, second and third paper rolls having a longitudinal length that is greater than a diameter or width of said first, second and third paper rolls, and wherein said paper rods substantially maintain their cross-section shape when forming said paper profile.

28. The paper profile as defined in claim 27, wherein each of said first, second and third paper rolls is formed of wood pulp and/or cellulose, said first, second and third paper rolls is absent adhesive.

29. The paper profile as defined in claim 27, including a shell element encircling said paper rods and forming an outer top, an outer bottom and outer side surface of said paper profile, said shell element formed of at least one layer of paper.

30. The paper profile as defined in claim 28, including a shell element encircling said paper rods and forming an outer top, an outer bottom and outer side surface of said paper profile, said shell element formed of at least one layer of paper.

31. The paper profile as defined in claim 29, wherein said shell element does not fully overlie said first end and second end of said paper profile.

32. The paper profile as defined in claim 30, wherein said shell element does not fully overlie said first end and second end of said paper profile.

33. The paper profile as defined in claim 27, wherein a separate adhesive is not used to secure together said paper rods.

34. The paper profile as defined in claim 32, wherein a separate adhesive is not used to secure together said paper rods.

35. The paper profile as defined in claim 27, including fourth and fifth paper rolls; said fourth and fifth paper rolls having a different cross sectional shape from said cross-section shape of said first, second and third paper rolls; said fourth and fifth paper rolls have substantially no hollow spaces, each of said fourth and fifth paper rolls is formed of a rolled-up web of paper, said each of said first, second and third paper rolls has substantially no hollow spaces prior to being used in said paper profile; said fourth and fifth paper rolls have a same cross-sectional size and profile along a longitudinal length of said paper rods, said cross section shape of said fourth and fifth paper rolls in a final form of said paper profile is selected from the group consisting of a circular shape, oval shape and stadium shape, each of said fourth and fifth paper rolls having a longitudinal length that is greater than a diameter or width of said fourth and fifth paper rolls.

36. The paper profile as defined in claim 34, including fourth and fifth paper rolls; said fourth and fifth paper rolls having a different cross sectional shape from said cross-section shape of said first, second and third paper rolls; said fourth and fifth paper rolls have substantially no hollow spaces, each of said fourth and fifth paper rolls is formed of a rolled-up web of paper, said each of said first, second and third paper rolls has substantially no hollow spaces prior to being used in said paper profile; said fourth and fifth paper rolls have a same cross-sectional size and profile along a longitudinal length of said paper rods, said cross section shape of said fourth and fifth paper rolls in a final form of said paper profile is selected from the group consisting of a circular shape, oval shape and stadium shape, each of said fourth and fifth paper rolls having a longitudinal length that is greater than a diameter or width of said fourth and fifth paper rolls.

* * * * *